US008093371B2

(12) United States Patent
Maeta et al.

(10) Patent No.: US 8,093,371 B2
(45) Date of Patent: Jan. 10, 2012

(54) METHOD OF PRODUCING A NUCLEIC ACID

(75) Inventors: Eri Maeta, Ibaraki (JP); Kenjiro Mori, Ibaraki (JP); Tatsuya Konishi, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 291 days.

(21) Appl. No.: 12/488,971

(22) Filed: Jun. 22, 2009

(65) Prior Publication Data

US 2009/0325233 A1 Dec. 31, 2009

(30) Foreign Application Priority Data

Jun. 25, 2008 (JP) ................................ 2008-165381

(51) Int. Cl.
*C07H 21/00* (2006.01)
*C12Q 1/68* (2006.01)
*C12P 19/34* (2006.01)

(52) U.S. Cl. ...... 536/25.3; 435/6.1; 435/91.1; 435/91.2; 435/91.5

(58) Field of Classification Search ................. 536/25.3; 435/6, 91.1, 91.2, 91.5, 6.1
See application file for complete search history.

(56) References Cited

U.S. PATENT DOCUMENTS

| | | | | | |
|---|---|---|---|---|---|
| 4,415,732 | A | * | 11/1983 | Caruthers et al. | 536/26.5 |
| 4,458,066 | A | * | 7/1984 | Caruthers et al. | 536/25.34 |
| 4,500,707 | A | * | 2/1985 | Caruthers et al. | 536/25.34 |
| 4,973,679 | A | * | 11/1990 | Caruthers et al. | 536/26.71 |
| 5,132,418 | A | * | 7/1992 | Caruthers et al. | 536/25.3 |
| 5,141,813 | A | | 8/1992 | Nelson | 428/402 |
| 5,262,530 | A | * | 11/1993 | Andrus et al. | 536/25.31 |
| 5,641,658 | A | * | 6/1997 | Adams et al. | 435/91.2 |
| 5,645,987 | A | * | 7/1997 | Richards | 435/6 |
| 5,700,920 | A | * | 12/1997 | Altmann et al. | 536/22.1 |
| 5,750,673 | A | * | 5/1998 | Martin | 536/26.1 |
| 5,869,696 | A | * | 2/1999 | Reddy et al. | 548/564 |
| 6,090,592 | A | * | 7/2000 | Adams et al. | 435/91.2 |
| 6,255,476 | B1 | * | 7/2001 | Vinayak et al. | 536/25.32 |
| 6,274,351 | B1 | * | 8/2001 | Peponnet | 435/91.1 |
| 6,297,016 | B1 | * | 10/2001 | Egholm et al. | 435/6 |
| 6,590,092 | B1 | * | 7/2003 | Ngo | 506/16 |
| 6,835,827 | B2 | * | 12/2004 | Vinayak et al. | 536/25.3 |
| 7,312,038 | B2 | * | 12/2007 | Rothschild et al. | 435/6 |
| 7,427,678 | B2 | * | 9/2008 | Pieken et al. | 536/25.3 |
| 7,439,341 | B2 | * | 10/2008 | Laikhter et al. | 534/727 |
| 7,521,541 | B2 | * | 4/2009 | Eigenbrot et al. | 530/387.1 |
| 7,635,772 | B2 | * | 12/2009 | McCormac | 536/25.31 |
| 2001/0024788 | A1 | * | 9/2001 | Hashimoto | 435/6 |
| 2004/0152905 | A1 | * | 8/2004 | Guzaev et al. | 548/453 |
| 2005/0054742 | A1 | | 3/2005 | Mori et al. | |
| 2005/0256285 | A1 | | 11/2005 | Mori et al. | |
| 2008/0064867 | A1 | | 3/2008 | Leuck et al. | |
| 2010/0168205 | A1 | * | 7/2010 | Meyers et al. | 514/44 A |

FOREIGN PATENT DOCUMENTS

| | | |
|---|---|---|
| EP | 1 721 908 A1 | 11/2006 |
| JP | 2005-097545 A | 4/2005 |
| JP | 2005-325272 A | 11/2005 |
| JP | 2006-342245 A | 12/2006 |
| JP | 2008-074979 A | 4/2008 |

OTHER PUBLICATIONS

Beaucage, S. L.; Iyer, R. P. Advances in the synthesis of oligonucleotides by the phosphoramidite approach. Tetrahedron 48 (12) : 2223-2311 (1992).*
Damha et al., An improved procedure for derivatization of controlled-pore glass beads for solid-phase oligonucleotide synthesis. Nucleic Acids Research 18 (13) : 3813 (1990).*
Maskos et al., Oligonucleotide hybridizations on glass supports: a novel linker for oligonucleotide synthesis and hybridization properties of oligonucleotides synthesised in situ. Nucleic Acids Research 20(7) : 1679 (1992).*
Sharma et al., One pot general method for the derivatisation of polymer support for oligonucleotide synthesis. Nucleic Acids Research 20(15) : 4100 (1992).*
Stamm et al., Sanchored PCR: PCR with cDNA coupled to a solid phase. Nucleic Acids Research 19(6) :1350 (1991).*
White HA., Ch.14 : Manual oligonucleotide synthesis using the Phosphoramidite method. Methods in Molecular Biology 4: 193(1988).*
Pon et al.,Derivatization of Controlled Pore Glass Beads for Solid Phase Oligonucleotide Synthesis. Biotechniques 6(8) :768-end of article (1988).*

* cited by examiner

*Primary Examiner* — Ethan C Whisenant

(74) *Attorney, Agent, or Firm* — Leydig, Voit & Mayer, Ltd.

(57) ABSTRACT

The present invention provides a method of producing a nucleic acid at high reaction efficiency and high reproducibility with a decreased variation in yield and purity among different reaction lots. A nucleic acid synthesis reaction is carried out on a first solid phase carrier capable of supporting nucleic acid synthesis contained in a solid phase carrier mixture comprising the first solid phase carrier and a second solid phase carrier that does not support nucleic acid synthesis.

6 Claims, No Drawings

METHOD OF PRODUCING A NUCLEIC ACID

TECHNICAL FIELD

The present invention relates to a method of producing a nucleic acid using a solid phase carrier.

BACKGROUND ART

Various methods of nucleic acid synthesis are available, many of which are based on a synthesis scheme wherein nucleosides are bound to a solid phase carrier, and nucleotides are sequentially bound to the nucleosides, whereby an elongated oligonucleotide is obtained.

Known solid phase carriers for the nucleic acid synthesis include polystyrene solid phase carriers, glass porous solid phase carriers and the like. Patent document 1 discloses a solid phase carrier consisting of a styrene-hydroxystyrene-divinylbenzene copolymer having a hydroxyl group as a functional group that contributes to nucleic acid synthesis. However, the document does not disclose or suggest using another solid phase carrier that does not support nucleic acid synthesis in a nucleic acid synthesis reaction.

In conventional methods of producing a nucleic acid utilizing a nucleic acid synthesis reaction on a solid phase carrier, there have been problems of wide variation in yield and purity among different reaction lots, and of low reaction efficiency and low reproducibility.

Patent document 1: JP-A-2005-97545

SUMMARY OF THE INVENTION

Technical Problem

In view of the above-mentioned problems, the present invention is directed to providing a method of producing a nucleic acid utilizing a nucleic acid synthesis reaction on a solid phase carrier, with decreased variation in yield and purity among different reaction lots, and with high reaction efficiency and high reproducibility.

Solution to Problem

The present inventors found that the above-mentioned problems could be solved by mixing a first solid phase carrier capable of supporting nucleic acid synthesis and a second solid phase carrier that does not support nucleic acid synthesis, and carrying out a nucleic acid synthesis reaction on the first solid phase carrier, and have developed the present invention.

Accordingly, the present invention relates to the aspects shown below.

[1] A method of producing a nucleic acid, comprising carrying out a nucleic acid synthesis reaction on a first solid phase carrier capable of supporting nucleic acid synthesis contained in a solid phase carrier mixture comprising the first solid phase carrier and a second solid phase carrier that does not support nucleic acid synthesis.

[2] The method of production according to [1] above, wherein the second solid phase carrier is contained in the solid phase carrier mixture at 1 to 50 parts by dry weight relative to 1 part by dry weight of the first solid phase carrier.

[3] The method of production according to [1] above, wherein the first solid phase carrier is any one selected from the group consisting of polystyrene solid phase carriers and glass porous solid phase carriers, and having a functional group that contributes to nucleic acid synthesis.

[4] The method of production according to [1] above, wherein the second solid phase carrier is any one selected from the group consisting of polystyrene solid phase carriers and glass porous solid phase carriers, and having substantially no functional group that contributes to nucleic acid synthesis.

[5] The method of production according to [1] above, wherein the nucleic acid synthesis reaction is carried out by the solid phase phosphoramidite method.

[6] The method of production according to [1] above, wherein the nucleic acid synthesis reaction is carried out in a container, and the apparent volume of the solid phase carrier mixture in a swollen state is 25 to 100% by volume of the inner volume of the container.

Advantageous Effect of the Invention

The method of the present invention enables synthesis of a nucleic acid at high efficiency and high reproducibility with decreased variation in yield and purity among different reaction lots.

DESCRIPTION OF EMBODIMENTS

The present invention relates to a method of producing a nucleic acid, comprising carrying out a nucleic acid synthesis reaction on a first solid phase carrier capable of supporting nucleic acid synthesis contained in a solid phase carrier mixture comprising the first solid phase carrier and a second solid phase carrier that does not support nucleic acid synthesis.

The term nucleic acid as used herein refers to a linear compound (oligonucleotide) wherein nucleotides are connected via phosphodiester bonds, and is understood to encompass DNA, RNA and the like. The nucleic acid may be single-stranded or double-stranded. Because it allows the efficient synthesis using a nucleic acid synthesizer, the nucleic acid is preferably single-stranded.

The nucleotide length of the nucleic acid is not particularly limited, and the nucleic acid is preferably 2 to 200 nucleotides long. If the nucleic acid is too long, the yield and purity of the nucleic acid obtained decrease.

The first solid phase carrier used in the method of the present invention is capable of supporting nucleic acid synthesis. "Capable of supporting nucleic acid synthesis" means the capability of solid phase nucleic acid synthesis on a carrier surface. The first solid phase carrier may be any solid phase carrier capable of supporting nucleic acid synthesis known per se. For example, polystyrene solid phase carriers, glass porous solid phase carriers and the like are used as first solid phase carriers. Because of higher nucleic acid yields compared with glass porous solid phase carriers, polystyrene solid phase carriers are preferably used as first solid phase carriers.

A polystyrene solid phase carrier refers to a solid phase carrier comprising (or consisting of) a copolymer containing the following structural unit (A):

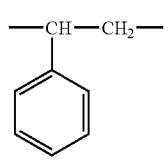

(A)

and/or a substitution derivative thereof as a structural unit. Substitution derivatives of the structural unit (A) include compounds wherein one or more hydrogen atoms contained in the structural unit (A) are substituted by an C1-5 alkyl group, halogen atom, amino group, hydroxyl group, carboxyl group, sulfonic acid group, cyano group, methoxy group, nitro group, vinyl group or the like. The substituent is preferably a hydroxyl group or an amino group. The position of the substituent is not particularly limited, and is preferably the para-position with respect to the main chain on the benzene ring. A preferable substitution derivative of the structural unit (A) is the structural unit (B) shown below.

(B)

The amount of structural unit (A) and/or substitution derivative thereof relative to the total amount of the structural units contained in the copolymer constituting the polystyrene solid phase carrier is not particularly limited, and is generally 50 to 100% by weight, preferably 60 to 100% by weight.

Examples of preferable polystyrene solid phase carriers include solid phase carriers consisting of a styrene-hydroxystyrene-divinylbenzene copolymer (JP-A-2005-097545, JP-A-2005-325272 and JP-A-2006-342245) and a solid phase carrier consisting of a styrene-(meth)acrylonitrile-hydroxystyrene-divinylbenzene copolymer (JP-A-2008-074979).

A glass solid phase carrier refers to a solid phase carrier comprising glass as a constituent.

A preferable first solid phase carrier is one having a functional group that contributes to nucleic acid synthesis. "Contributes to nucleic acid synthesis" means serving as a starting point for a nucleic acid synthesis reaction. Specific examples of such functional groups include amino groups, hydroxyl groups, carboxyl groups, sulfonic acid groups and the like. Preferable functional groups are amino groups, hydroxyl groups and the like, which permit the addition of a linker.

The content of the functional group that contributes to nucleic acid synthesis contained in the first solid phase carrier is not particularly limited, and is preferably within the range of 10 to 1000 µmol/g, more preferably 50 to 500 µmol/g. If the functional group content is too low, nucleic acid yield decreases. If the functional group content is too high, the purity of the nucleic acid obtained tends to decrease. More specifically, too high a content of the functional group is likely to result in a smaller-than-desired number of nucleotides in the nucleic acid obtained.

When the functional group that contributes to nucleic acid synthesis is a hydroxyl group, the hydroxyl group content in the solid phase carrier is determined by a titration in compliance with the JIS K0070. Specifically, the measurement target hydroxyl group in a carrier for solid phase synthesis is acetylated with a predetermined amount of an acetylation reagent (acetic anhydride or pyridine), the amount of acetic anhydride that has not been consumed during the acetylation is determined by titration with potassium hydroxide, and the amino group content or hydroxyl group content is calculated. The specific procedures are shown below.

Pyridine is added to 25 g of acetic anhydride to make a total volume of 100 ml to obtain an acetylation reagent. A sample (dry solid phase carrier), 0.5 to 2 g, is weighed out in a flask, and 0.5 ml of the above-mentioned acetylation reagent and 4.5 ml of pyridine are added accurately. After being kept at 95 to 100° C. for 2 hr, the mixture in the flask is allowed to cool to room temperature, after which 1 ml of distilled water was added. The flask was heated for 10 min. to decompose the acetic anhydride that has not been consumed in the acetylation. All content in the flask is transferred to a beaker, and diluted with distilled water to make a total volume of 150 ml, after which the dilution is titrated with a 0.5 mol/l aqueous potassium hydroxide solution.

Separately, a blank measurement is performed in the same way, but without adding the sample.

The hydroxyl group content of the sample is calculated by the formula (1) below:

$$A=(B-C)\times 0.5(\text{mol/l})\times f\times 1000\div M \quad (1)$$

where A (µmol/g) is the hydroxyl group content of the sample;

B (ml) is the amount of aqueous potassium hydroxide solution added to neutralize the blank solution;

C (ml) is the amount of aqueous potassium hydroxide solution added to neutralize the sample;

f is a factor for the aqueous potassium hydroxide solution;

M (g) is the weight of the sample weighed out.

The first solid phase carrier may have a linker bound thereto. The linker is preferably bound to a functional group that contributes to nucleic acid synthesis on the first solid phase carrier. A linker refers to a molecule that joins together two molecules via a covalent bond. In the present invention, the linker joins the first solid phase carrier and a nucleic acid. Useful linkers include those known per se in use to join a carrier and a nucleic acid in solid phase nucleic acid synthesis. Preferable linkers include a nucleoside-succinyl linker represented by the formula below:

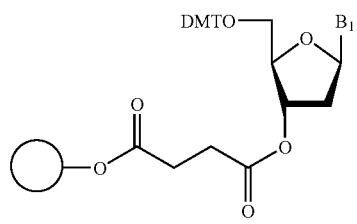

O ... Carrier for solid phase synthesis
DMT ... 5' OH protecting group
$B_1$ ... base The amount of linker bound to the first solid phase carrier is not particularly limited, and is generally within the range of 20 to 500 µmol/g. If the linker content is too low, the yield of nucleic acid decreases. If the linker content is too high, the purity of the nucleic acid obtained tends to decrease. More specifically, too high a linker content is likely to result in a smaller-than-desired number of nucleotides in the nucleic acid obtained.

The surface or inner shape of the first solid phase carrier is not particularly limited; any surface or inner shape of a solid phase carrier generally used in nucleic acid solid phase synthesis is applicable, without limitations, to the first solid phase carrier. For example, the specific surface area as determined by the BET method is preferably in the range of 10 to 300 m²/g. When a solid phase carrier with too small a specific surface area is used, it is feared that the chemical synthesis reaction field decreases, resulting in a decreased yield of nucleic acid obtained. Conversely, a large specific surface area of a solid phase carrier can indicate two cases: one wherein many fine pores have been formed and the other wherein the porosity has increased. If there are too many fine pores, it is feared that the progress of the synthesis reaction is hampered when the solid phase carrier is used. If the porosity is too high, the physical strength of the solid phase carrier decreases, which in turn can break the beads during the synthesis operation.

As mentioned herein, the specific surface area of a solid phase carrier is determined by the BET method.

A measurement by the BET method is performed with gaseous nitrogen as an adsorption gas, using the specific surface area analyzer NOVA 1200 (QuantaChrome). A sample is placed in the apparatus and deaerated at room temperature in a vacuum for 120 minutes, thereafter the specific surface area of the sample is determined by the BET multipoint method.

The shape of the first solid phase carrier is not particularly limited, and is preferably a shape of a particle. The term particle does not mean being exactly spherical, but means having any constant form (e.g., roughly spherical forms such as ellipse spherical, polygonal form, cylindrical form, irregular forms such as konpeito form, and the like). It is preferable that the shape of the first solid phase carrier be roughly spherical (most preferably spherical) because this allows an increase in the efficiency of filling in the synthesis reaction vessel, and also because this is unlikely to break the reaction vessel. The size (volume) of the particle is not particularly limited, and the median particle diameter is preferably 1 to 1000 μm, more preferably 5 to 500 μm, and still more preferably 10 to 200 μm.

As mentioned herein, the median particle diameter of a solid phase carrier is expressed as a value obtained by dispersing the solid phase carrier in $EtOH/H_2O=50/50$ (ratio by volume), sonicating for 10 minutes to cause further dispersion, and thereafter analyzing using the HORIBA laser diffraction/scattering particle distribution analyzer (LA-920).

From the viewpoint of increasing the reaction field, the first solid phase carrier is preferably porous. When the first solid phase carrier is porous, the pore size, the number of pores and the like are not particularly limited; any pore size, number of pores and the like of the porous solid phase carrier generally used in nucleic acid solid phase synthesis are applicable, without limitations, to the first solid phase carrier. Pore size can be quantified as a median pore size; an example of a preferable range of median pore diameter of the first solid phase carrier is 0.1 to 1000 nm. If the median pore diameter of the first solid phase carrier is too small, it is feared that the field of reaction decreases to an extent making the desired reaction unlikely to occur, and that the base number of a base sequence involved in the oligonucleotide synthesis tends to be smaller than desired. Conversely, if the median pore diameter of the first solid phase carrier is too large, the chance of contact of the functional group (e.g., hydroxyl group) on the above-mentioned carrier surface being the reaction field and the substances involved in the reaction can decrease, a disadvantage for a carrier.

In the present specification, the median pore diameter of the solid phase carrier is determined by mercury porosimetry. Specifically, an about 0.2 g sample is placed in the mercury porosimeter PoreMaster 60-GT (QuantaChrome Co.), and measurements are performed by the mercury injecting pressurization method under the condition of a mercury contact angle of 140° and a mercury surface tension of 480 dyn/cm.

The method of preparing a first solid phase carrier is not particularly limited; a method known per se can be used. For example, a solid phase carrier consisting of a styrene-hydroxystyrene-divinylbenzene copolymer can be produced by the method disclosed in JP-A-2005-097545, JP-A-2005-325272 or JP-A-2006-342245. A solid phase carrier consisting of a styrene-(meth)acrylonitrile-hydroxystyrene-divinylbenzene copolymer can be produced by the method disclosed in JP-A-2008-074979.

Described below is a typical method wherein a styrene monomer, an acyloxystyrene monomer and a divinylbenzene monomer are suspension-copolymerized using an organic solvent and water to yield a styrene-acyloxystyrene-divinylbenzene copolymer, which copolymer is hydrolyzed to produce a styrene-hydroxystyrene-divinylbenzene copolymer.

The styrene monomer is styrene or a substitution derivative thereof, and is preferably styrene. As the substitution derivative of styrene, a compound wherein one or more hydrogen atoms of styrene are substituted by a C1-5 alkyl group, halogen atom, amino group, carboxyl group, sulfo group, cyano group, methoxy group, nitro group or the like, can be mentioned.

The acyloxystyrene monomer is acyloxystyrene or a substitution derivative thereof, and is preferably unsubstituted p-acetoxystyrene. As the substitution derivative of acyloxystyrene, a compound wherein one or more hydrogen atoms, other than those in the acyloxy group, are substituted by a C1-5 alkyl group, halogen atom, amino group, carboxyl group, sulfo group, cyano group, methoxy group, nitro group or the like, can be mentioned. The acyloxy group is preferably a C1-5 acyloxy group, more preferably an acetoxy group. It is preferable that the acyloxy group be present at the para-position with respect to the vinyl group.

The divinylbenzene monomer is divinylbenzene or a substitution derivative thereof, and is preferably divinylbenzene. As the substitution derivative of divinylbenzene, a compound wherein one or more hydrogen atoms are substituted by a C1-5 alkyl group, halogen atom, amino group, carboxyl group, sulfo group, cyano group, methoxy group, nitro group or the like, can be mentioned.

During the suspension copolymerization, the amount of acyloxystyrene monomer relative to the total amount of styrene monomer, acyloxystyrene monomer and divinylbenzene monomer is 0.2 to 20% by weight, preferably 1 to 15% by weight, and more preferably 2 to 8% by weight.

During the suspension copolymerization, the amount of divinylbenzene monomer relative to the total amount of styrene monomer, acyloxystyrene monomer and divinylbenzene monomer is not particularly limited, and is preferably 4 to 35% by weight, more preferably 5 to 25% by weight.

In a preferred embodiment, a system comprising styrene, p-acetoxystyrene, and divinylbenzene as monomers is subjected to the aforementioned process of suspension copolymerization. Here, the two vinyl groups of the divinylbenzene are mutually at the para- or meta-position. In the suspension copolymerization, relative to the total amount of styrene, p-acetoxystyrene and divinylbenzene, styrene preferably accounts for 60 to 95% by weight, more preferably 70 to 90% by weight; p-acetoxystyrene preferably accounts for 0.2 to 20% by weight, more preferably 1 to 15% by weight; divinylbenzene preferably accounts for 4 to 35% by weight, more preferably 5 to 25% by weight. The amount of one or two of the styrene, p-acetoxystyrene and divinylbenzene may be within the above-mentioned range; particularly preferably, the amounts of all these three monomers fall within the above-mentioned respective ranges.

The suspension copolymerization is performed by stirring the aforementioned monomers and an organic solvent in water. As used herein, the term "organic solvent" refers to a solvent, other than water, in a suspension copolymerization system. In the present invention, the above-mentioned organic solvent includes hydrocarbons and alcohols. Useful hydrocarbons include aliphatic saturated or unsaturated hydrocarbons and aromatic hydrocarbons, with preference given to aliphatic hydrocarbons having 5 to 12 carbon atoms, more preferably to n-hexane, n-heptane, n-octane, isooctane, undecane, dodecane and the like. The presence of an alcohol during suspension copolymerization makes the obtained beads porous. Examples of the alcohols include aliphatic alcohols, the number of carbon atoms in the alkyl group thereof being preferably 5 to 12; more preferable alcohols include 2-ethylhexylalcohol, t-amyl alcohol, nonyl alcohol, 2-octanol, decanol, lauryl alcohol, cyclohexanol and the like.

During suspension copolymerization, the amount of organic solvent relative to the total amount of monomers (organic solvent/monomer), by weight, is preferably 0.5 to 2.0, more preferably 0.8 to 1.5. During the suspension copolymerization, the weight ratio of the hydrocarbon to the alcohol is changed as appropriate according to the specific combination of the hydrocarbon and alcohol. For example, when isooctane and 2-ethylhexanol are used, it is preferable, from the viewpoint of increasing the specific surface area of the obtained porous resin beads, that the weight ratio thereof (isooctane/2-ethylhexanol) be 1/9 to 6/4.

The suspension copolymerization may be performed by a conventional known method. For example, during the suspension copolymerization, known dispersion stabilizers such as polyvinyl alcohol and peroxides (polymerization initiators) such as benzoyl peroxide can be used. Reaction conditions for the suspension copolymerization can be set as appropriate; for example, stirring at 60 to 90° C. for 30 minutes to 24 hours can be mentioned. By this suspension copolymerization, a styrene-acyloxystyrene-divinylbenzene copolymer can be obtained. The copolymer obtained is appropriately washed, classified and the like, and then subjected to the hydrolyzing treatment described below.

Hydrolysis to convert the acyloxy groups to hydroxyl groups in the styrene-acyloxystyrene-divinylbenzene copolymer can be achieved using commonly known procedures and conditions, wherein an acid or alkali catalyst may be used. Specific examples of the hydrolysis are described in Examples below. In the method of the present invention, it is not always necessary that all acyloxy groups be converted to hydroxyl groups (100% degree of hydrolysis). This is followed by the treatments shown below, whereby the first solid phase carrier can be obtained. During production thereof, drying, size classification and other treatments may be performed.

The second solid phase carrier used in the method of the present invention substantially does not support nucleic acid synthesis. "Substantially does not support nucleic acid synthesis" means that substantially no solid phase synthesis of nucleic acid occurs on a carrier surface.

To ensure that substantially no solid phase synthesis of nucleic acid occurs on the second solid phase carrier surface, the content of the functional group that contributes to nucleic acid synthesis, contained in the second solid phase carrier, is generally 0 to 10 µmol/g, preferably substantially 0 µmol/g (that is, the solid phase carrier substantially does not have a functional group that contributes to nucleic acid synthesis).

In a preferred embodiment, a solid phase carrier mixture of the first solid phase carrier and the second solid phase carrier which are mixed substantially uniformly is used as described below. Accordingly, to facilitate the uniform mixing of solid phase carriers, it is preferable that the properties of the second solid phase carrier be as identical as possible to the properties of the first solid phase carrier except for the content of the functional group that contributes to nucleic acid synthesis. As mentioned herein, the properties of a solid phase carriers include the kind of the copolymer constituting the solid phase carrier; degree of crosslinking; shape; specific surface area; median particle diameter; presence or absence of pores, pore size, and the number of pores.

The choice of second solid phase carrier is not particularly limited, as far as it substantially does not support nucleic acid synthesis; a solid phase carrier known per se can be used. For example, a polystyrene solid phase carrier, a glass porous solid phase carrier and the like can be used. As a second solid phase carrier, a polystyrene solid phase carrier is preferably used.

Although the definition of a polystyrene solid phase carrier is as described above, to minimize the content of the functional group that contributes to nucleic acid synthesis, it is preferable that the structural unit of the copolymer constituting the solid phase carrier be free from a structural unit (A) substituted by a functional group that contributes to nucleic acid synthesis (amino group, hydroxyl group, carboxyl group, sulfonic acid group etc.).

The amount of styrene and/or substitution derivative thereof relative to the total amount of structural units contained in the copolymer constituting the polystyrene solid phase carrier used as a second solid phase carrier is not particularly limited, and is generally 50 to 100% by weight, preferably 60 to 100% by weight.

Preferable polystyrene solid phase carriers include a solid phase carrier consisting of a styrene-divinylbenzene copolymer, a solid phase carrier consisting of a styrene-(meth)acrylonitrile-divinylbenzene copolymer and the like. Examples of styrene-divinylbenzene copolymers include the solid phase carriers consisting of a styrene-hydroxystyrene-divinylbenzene copolymer disclosed in JP-A-2005-097545, JP-A-2005-325272 and JP-A-2006-342245 except that all hydroxystyrene being the structural unit is replaced with unsubstituted styrene. Examples of solid phase carriers consisting of a styrene-(meth)acrylonitrile-divinylbenzene copolymer include the solid phase carrier consisting of a styrene-(meth)acrylonitrile-hydroxystyrene-divinylbenzene copolymer disclosed in JP-A-2008-074979 except that all hydroxystyrene being the structural unit is replaced with unsubstituted styrene.

The surface or inner shape of the second solid phase carrier is not particularly limited. For example, the specific surface area as determined by the BET method is preferably in the range of 10 to 300 m$^2$/g.

The shape of the second solid phase carrier is not particularly limited, and is preferably a shape of a particle. The term particle does not mean being exactly spherical, but means having any constant form (e.g., roughly spherical forms such as ellipse spherical, polygonal form, cylindrical form, irregular forms such as konpeito form, and the like). It is preferable that the shape of the second solid phase carrier be roughly spherical (most preferably spherical) because this allows an increase in the efficiency of filling in the synthesis reaction vessel, and also because this is unlikely to break the reaction vessel. The size (volume) of the particle is not particularly limited, and the median particle diameter is preferably 1 to 1000 µm, more preferably 5 to 500 µm, and still more preferably 10 to 200 µm.

When the first and second solid phase carriers are roughly spherical, the median particle diameter of the first solid phase carrier is within the range of generally 0.1 to 10 times, preferably 0.3 to 3 times, the median particle diameter of the second solid phase carrier. This is because the first and second solid phase carriers are likely to mix uniformly.

The second solid phase carrier is preferably porous. If the second solid phase carrier is porous, the pore size, the number of pores and the like are not particularly limited. The pore size can be quantified as median pore diameter; a preferable range of the median pore diameter of the second solid phase carrier is 0.1 to 1000 nm.

A second solid phase carrier can be produced according to the aforementioned method of producing a first solid phase carrier. For example, a solid phase carrier consisting of a styrene-divinylbenzene copolymer can be produced by one of the methods of producing a solid phase carrier consisting of a styrene-hydroxystyrene-divinylbenzene copolymer, the methods described above or disclosed in JP-A-2005-097545, JP-A-2005-325272 and JP-A-2006-342245, using an unsubstituted styrene monomer in place of acyloxystyrene monomer in the copolymerization reaction. A solid phase carrier consisting of a styrene-(meth)acrylonitrile-divinylbenzene copolymer can be produced by the method of producing a solid phase carrier consisting of styrene-(meth)acrylonitrile-hydroxystyrene-divinylbenzene copolymer, disclosed in JP-A-2008-074979, using an unsubstituted styrene monomer in place of acyloxystyrene monomer in the copolymerization reaction.

A second solid phase carrier can also be produced by capping the functional group that contributes to nucleic acid synthesis, contained in the first solid phase carrier, using a capping reagent. Specifically, when the functional group is a hydroxyl group or an amino group, acetic anhydride/tetrahydrofuran solution, N-methylimidazole/tetrahydrofuran solution and the like can be used as a capping reagent.

The ratio (by dry weight) of the first and second solid phase carriers contained in the solid phase carrier mixture used in the method of the present invention is generally 70 to 100%, preferably 90 to 100%, and most preferably substantially 100%. Accordingly, in the most preferred embodiment, the solid phase carrier mixture used in the method of the present invention consists of the first solid phase carrier and the second solid phase carrier. The properties of any solid phase carrier other than the first and second solid phase carriers contained in the solid phase carrier mixture used in the method of the present invention is not particularly limited, as far as the nucleic acid synthesis reaction is not interfered with; preferably, the properties of the solid phase carrier are determined within the aforementioned range of the properties of the first or second solid phase carrier.

The content ratio between the first and second solid phase carriers in the solid phase carrier mixture used in the method of the present invention is not particularly limited; generally, the second solid phase carrier is contained at 1 to 50 parts by weight (dry weight, the same applied below), preferably 1 to 25 parts by weight, more preferably 1 to 10 parts by weight, and most preferably 1 to 5 parts by weight, relative to 1 part by weight (dry weight) of the first solid phase carrier. If the amount of the second solid phase carrier is too small, the desired effect of increasing the reaction efficiency and reproducibility of the nucleic acid synthesis is unlikely to achieve. Conversely, if the amount of the second solid phase carrier is too large, it is feared that the yield of the nucleic acid obtained finally decreases.

A solid phase carrier mixture used in the method of the present invention can be produced by weighing out a first solid phase carrier and a second solid phase carrier, and stirring them in a vial using a vortex, rotor and the like. From the viewpoint of ensuring a sufficient reproducibility of the yield and purify of the nucleic acid obtained, it is preferable that the first and second solid phase carriers be mixed substantially uniformly.

Production of a nucleic acid by the method of the present invention is generally carried out in a container filled with a solid phase carrier mixture comprising a first solid phase carrier and a second solid phase carrier. Usually, the solid phase carrier mixture is filled in the container in a way such that the adjacent solid phase carriers can be in physical contact with each other while standing. Preferably, the solid phase carrier mixture after swelling with a solvent (particularly toluene) used in the nucleic acid synthesis reaction is filled so that the total apparent volume thereof will be 25 to 100% of the inner volume of the container. As mentioned herein, an apparent volume refers to a volume measured using a graduated cylinder after the solid phase carrier is swollen with toluene for 24 hours.

In the method of the present invention, a nucleic acid synthesis reaction is carried out on a first solid phase carrier contained in a solid phase carrier mixture.

As mentioned herein, a nucleic acid synthesis reaction particularly means a nucleic acid elongation reaction. Hence, nucleotides are sequentially bound to a nucleoside, nucleotide or oligonucleotide bound to the first solid phase carrier, whereby an elongated oligonucleotide is obtained.

In the method of the present invention, various solid phase nucleic acid synthesis reactions known per se can be used. A nucleic acid synthesis reaction can be performed by the H-phosphonate method, phosphoester method, solid phase phosphoramidite method and the like. In particular, the solid phase phosphoramidite method is preferable because of high capacity of synthesizing nucleic acid and high purity of nucleic acid obtained. This is described in U.S. Pat. No. 4,458,066 titled "PROCESS FOR PREPARING POLYNUCLEOTIDES" issued to Caruthers et al. For example, a synthesis cycle comprising the following four steps for binding a nucleotide is performed on the first solid phase carrier:

(1) detritylation with dichloroacetic acid and the like to remove DMT being the protecting group for the 5'-OH of the nucleoside succinyl linker bound to the beads;
(2) coupling to bind a nucleoside phosphoramidite activated by tetrazole and the like to the aforementioned 5'-OH;
(3) capping to protect the 5'-OH to which the amidite has not bound, with acetic anhydride and the like; and
(4) oxidation with iodine and the like to have a phosphoric acid triester.

Nucleic acid production can be automated by connecting a reaction vessel (column etc.) filled with a solid phase carrier mixture comprising a first solid phase carrier and a second solid phase carrier to an automated nucleic acid synthesizer incorporating a program for the steps of nucleic acid synthesis reaction. For example, as directed by the controller of the synthesizer or a computer, the individual steps are performed by a reagent dispensing system that dispenses reagents to a reaction vessel filled with a solid phase carrier mixture comprising a first solid phase carrier and a second solid phase carrier in a predetermined order, with the above-mentioned steps (1) to (4) being one cycle. After this cycle is repeated as many times as required to produce the desired product, the solid phase carrier bound with the synthesized nucleic acid (oligonucleotide) are taken out from the reaction vessel, and recovered in a vial. Concentrate ammonia and the like are added thereto, and the vessel is allowed to stand at 55° C. for 8 hours, whereby the succinyl linker is cleaved. The oligonucleotide is cut out from the first solid phase carrier; the cyanoethyl group is removed to obtain the phosphodiester; the amino-protecting group in the base moiety is removed. The steps of cutting out and deprotection are thus performed. Then, the oligonucleotide is isolated using a filter, whereby the desired nucleic acid is obtained.

EXAMPLES

The present invention is hereinafter described in further detail by means of the following examples, which, however, are not to be construed as limiting the scope of the invention.

Example 1

Production of First Solid Phase Carrier Capable of Supporting Nucleic Acid Synthesis (Porous Particles of Styrene/Hydroxystyrene/Divinylbenzene Copolymer: Solid Phase Carrier A)
(Suspension Copolymerization)

A 500 mL separable flask, equipped with a cooler, stirrer, and nitrogen inlet tube, was attached to a constant-temperature water chamber, and 240 g of purified water (Daiwa Pharmaceutical) and 2.4 g of polyvinyl alcohol (manufactured by KURARAY, average degree of polymerization=about 2000, saponification value 79 mol %) were placed therein. After adjusting the constant-temperature water chamber to a temperature of 28° C., the polyvinyl alcohol was dissolved with stirring.

Separately, 44 g of styrene (Wako Pure Chemical Industries), 3 g of p-acetoxystyrene (Tosoh Organic Chemical), and 7 g of 55% divinylbenzene (Wako Pure Chemical Industries) were mixed, and 1 g of dibenzoyl peroxide (NOF Corporation, 25% hydrated) was added and dissolved. This mixture was admixed with 50 g of 2-ethylhexanol (Kanto Chemical) and 20 g of isooctane (Wako Pure Chemical Industries), and the mixed solution was placed in the separable flask. After stirring in a nitrogen stream at 480 rpm for 40 minutes, the stirring rotation rate was decreased to 300 rpm, and the constant-temperature water chamber temperature was raised from 28° C. to 80° C.; a suspension copolymerization reaction was carried out for 9 hours.

After completion of the copolymerization reaction, the constant-temperature water chamber was adjusted to a decreased temperature, and the polymerization liquor was cooled to 28° C.
(Filtration)

The polymerization liquor was suction-filtered using a filter medium (manufactured by NRK, nylon-meshed, aperture=45 μm) to yield a cake of gathered porous polymer beads.
(Washing)

After adding 200 mL of purified water, the cake of gathered porous polymer beads was thoroughly dispersed with stirring. This was filtered again to yield a cake of gathered porous polymer beads. This operation was repeated in 4 cycles.

Furthermore, 200 mL of acetone (Wako Pure Chemical Industries) was added, and the cake of gathered porous polymer beads was washed and filtered in the same manner. This operation was repeated in 3 cycles.
(Addition of Hydroxyl Groups)

200 mL of ethanol was added into the cake of gathered porous polymer beads, and the cake was thoroughly dispersed with stirring. This was filtered again to yield a cake of gathered porous polymer beads. After adding 160 mL of ethanol and 40 mL of 1 mol/L sodium hydroxide solution, the cake was thoroughly dispersed with stirring; the dispersion was heated to 76° C. to perform hydrolysis reaction for 3 hours. After completion of the reaction, the product was cooled to room temperature and neutralized with 1 mol/L hydrochloric acid aqueous solution, after which the solution was filtered. This was followed by the steps in the same manner as described in the "Washing" section above.

(Drying)

The washed cake of gathered porous polymer beads was dried in a 70° C. vacuum dryer for 48 hours to yield gathered porous polymer beads of Example 1.
(Addition of Linker)

After DMT-dT-3'-succinate (nucleoside linker) was bound to each hydroxyl group of the gathered porous polymer beads of Example 1 with an adjustment to obtain a content of 0.2 mmol/g, the hydroxyl groups to which the nucleoside linker had not bound were capped with acetyl groups.

The solid phase carrier A thus obtained had the properties shown below:
Degree of crosslinking: 7%
Shape: spherical
Specific surface area: 45 $m^2/g$
Median particle diameter: 90 μm
Median pore diameter: 52 nm
Production of Second Solid Phase Carrier that does not Support Nucleic Acid Synthesis (Solid Phase Carrier B)
(Suspension Copolymerization)

A 500 mL separable flask, equipped with a cooler, stirrer, and nitrogen inlet tube, was attached to a constant-temperature water chamber, and 240 g of purified water (Daiwa Pharmaceutical) and 2.4 g of polyvinyl alcohol (manufactured by KURARAY, average degree of polymerization=about 2000, saponification value=79 mol %) were placed therein. After adjusting the constant-temperature water chamber to a temperature of 28° C., the polyvinyl alcohol was dissolved with stirring.

Separately, 47 g of styrene (Wako Pure Chemical Industries) and 7 g of divinylbenzene (Wako Pure Chemical Industries) were mixed, and 1 g of dibenzoyl peroxide (NOF Corporation, 25% hydrated) was added and dissolved. The resulting mixture was admixed with 50 g of 2-ethylhexanol (Kanto Chemical) and 20 g of isooctane (Wako Pure Chemical Industries), and the mixed solution was placed in the above-mentioned separable flask. After stirring in a nitrogen stream at 480 rpm for 40 minutes, the stirring rotation rate was decreased to 300 rpm, and the constant-temperature water chamber temperature was raised from 28° C. to 80° C.; a suspension copolymerization reaction was carried out for 9 hours.

After completion of the copolymerization reaction, the constant-temperature water chamber was adjusted to a decreased temperature, and the polymerization liquor was cooled to 28° C.
(Filtration)

The polymerization liquor was suction-filtered using a filter medium (manufactured by NRK, nylon-meshed, aperture=45 μm) to yield a cake of gathered porous polymer beads.
(Washing)

After adding 200 ml of purified water, the cake of gathered porous polymer beads was thoroughly dispersed with stirring. This was filtered again to yield a cake of gathered porous polymer beads. This operation was repeated in 4 cycles.

Furthermore, 200 ml of acetone (Wako Pure Chemical Industries) was added, and the cake of gathered porous polymer beads was washed and filtered in the same manner. This operation was repeated in 3 cycles.

The solid phase carrier B thus obtained had the properties shown below:
Degree of crosslinking: 7%
Shape: spherical
Specific surface area: 45 $m^2/g$
Median particle diameter: 90 μm
Median pore diameter: 52 nm (Synthesis of Nucleic Acids)

Single-stranded DNAs were synthesized using beads of a uniformly blended mixture of the solid phase carrier A and the solid phase carrier B in a 1:2 ratio by weight under conditions of 1 µmol (15 mg of solid phase mixture filled), 20 bases and DMT-on using the ABI3400 nucleic acid synthesizer (Applied Biosystems); their OD (optical density) values and HPLC (high performance liquid chromatography) purities were determined. The apparent volume of the solid phase carrier mixture in a toluene-swollen state was 71.1% of the inner volume of the reaction container.

The results are summarized below.

TABLE 1

| | Solid phase carrier A:solid phase carrier B (weight ratio) | Amount (mg) of solid phase carrier mixture filled | Synthesis scale (µmol) | OD | HPLC (%) |
|---|---|---|---|---|---|
| 1 | 1:2 | 15 | 1 | 131.00 | 73.96 |
| 2 | 1:2 | 15 | 1 | 120.83 | 72.47 |
| 3 | 1:2 | 15 | 1 | 117.83 | 76.17 |

Example 2

The same steps as Example 1 were followed except that the solid phase carrier A and the solid phase carrier B were blended in a 1:3 ratio by weight. The apparent volume of the solid phase carrier mixture in a toluene-swollen state was 94.8% of the inner volume of the reaction container.

The results are summarized below.

TABLE 2

| | Solid phase carrier A:solid phase carrier B (weight ratio) | Amount (mg) of solid phase carrier mixture filled | Synthesis scale (µmol) | OD | HPLC (%) |
|---|---|---|---|---|---|
| 1 | 1:3 | 20 | 1 | 175.33 | 83.00 |
| 2 | 1:3 | 20 | 1 | 179.17 | 82.90 |
| 3 | 1:3 | 20 | 1 | 185.00 | 82.30 |

Comparative Examples

Nucleic acids were synthesized using the solid phase carrier A and the solid phase carrier B in a 1:0 ratio by weight under the conditions of 1 µmol (5 mg of solid phase filled), 20 bases, and DMT-on; their OD values and HPLC purities were determined.

The results are summarized below.

TABLE 3

| | Solid phase carrier A:solid phase carrier B (weight ratio) | Amount (mg) of solid phase carrier mixture filled | Synthesis scale (µmol) | OD | HPLC (%) |
|---|---|---|---|---|---|
| 1 | 1:0 | 5 | 1 | 81.30 | 63.61 |
| 2 | 1:0 | 5 | 1 | 65.30 | 57.43 |
| 3 | 1:0 | 5 | 1 | 94.00 | 68.40 |

When nucleic acids were synthesized with the addition of a solid phase carrier that does not support nucleic acid synthesis, both the amount synthesized (OD) and the HPLC purity increased, and reproducible results were obtained.

INDUSTRIAL APPLICABILITY

The method of the present invention enables synthesis of a nucleic acid at high efficiency and high reproducibility with decreased variation in yield and purity among different reaction lots.

This application is based on a patent application No. 2008-165381 filed in Japan (filing date: Jun. 25, 2008), the contents of which are incorporated in full herein by this reference.

The invention claimed is:

1. A method of producing a nucleic acid, comprising carrying out a nucleic acid synthesis reaction on a first solid phase carrier capable of supporting nucleic acid synthesis contained in a solid phase carrier mixture comprising the first solid phase carrier and a second solid phase carrier that does not support nucleic acid synthesis.

2. The method of claim 1, wherein the second solid phase carrier is contained in the solid phase carrier mixture at 1 to 50 parts by dry weight relative to 1 part by dry weight of the first solid phase carrier.

3. The method of claim 1, wherein the first solid phase carrier is any one selected from the group consisting of polystyrene solid phase carriers and glass porous solid phase carriers, and having a functional group that contributes to nucleic acid synthesis.

4. The method of claim 1, wherein the second solid phase carrier is any one selected from the group consisting of polystyrene solid phase carriers and glass porous solid phase carriers, and having substantially no functional group that contributes to nucleic acid synthesis.

5. The method of claim 1, wherein the nucleic acid synthesis reaction is carried out by the solid phase phosphoramidite method.

6. The method of claim 1, wherein the nucleic acid synthesis reaction is carried out in a container, and the apparent volume of the solid phase carrier mixture in a swollen state is 25 to 100% by volume of the inner volume of the container.

* * * * *